United States Patent [19]
Thakur et al.

[11] Patent Number: 5,345,005
[45] Date of Patent: Sep. 6, 1994

[54] HYDROGENATION CATALYST, PROCESS FOR PREPARING AND PROCESS OF USING SAID CATALYST

[75] Inventors: Deepak S. Thakur; Brian L. Roberts, both of Solon; Thomas J. Sullivan, Strongsville; Anita L. Vichek, Mentor, all of Ohio

[73] Assignee: Engelhard Corporation, Iselin, N.J.

[21] Appl. No.: 930,123

[22] Filed: Sep. 18, 1992

Related U.S. Application Data

[60] Division of Ser. No. 680,100, Apr. 2, 1991, Pat. No. 5,155,086, which is a continuation-in-part of Ser. No. 422,624, Oct. 17, 1989, abandoned, which is a continuation-in-part of Ser. No. 405,983, Sep. 12, 1989, abandoned.

[51] Int. Cl.$^5$ .................. C07C 29/149; C07C 31/125
[52] U.S. Cl. .................... 568/885; 549/503; 568/811; 568/814; 568/864; 568/881
[58] Field of Search ............. 568/811, 814, 864, 881, 568/885; 549/503

[56] References Cited

U.S. PATENT DOCUMENTS

| | | | |
|---|---|---|---|
| 1,961,980 | 6/1934 | Mueller-Conradi et al. | 260/156.5 |
| 2,091,800 | 8/1937 | Adkins et al. | 260/156 |
| 2,105,664 | 1/1938 | Lazier | 260/153 |
| 2,118,001 | 5/1938 | Andrews et al. | 260/127 |
| 2,118,007 | 5/1938 | Covert et al. | 260/156 |
| 2,121,367 | 6/1938 | Schiller | 260/156 |
| 2,285,448 | 6/1942 | Loder | 260/635 |
| 2,325,206 | 7/1943 | Stengel | 260/635 |
| 2,327,189 | 8/1943 | Ipatieff et al. | 260/683 |
| 2,334,100 | 11/1943 | Ipatieff et al. | 260/668 |
| 2,444,509 | 7/1948 | Ipatieff et al. | 252/211.5 |
| 2,549,416 | 4/1951 | Brooks | 260/638 |
| 2,782,243 | 2/1957 | Hess et al. | 260/638 |
| 3,173,959 | 3/1965 | Rittmeister | 260/638 |
| 3,197,418 | 7/1965 | Maebashi et al. | 252/454 |
| 3,267,157 | 8/1966 | Miya | 260/638 |
| 3,388,972 | 6/1968 | Reitmeier et al. | 23/213 |
| 3,431,311 | 3/1969 | Cooper et al. | 260/638 |

(List continued on next page.)

FOREIGN PATENT DOCUMENTS

| | | |
|---|---|---|
| 0011150 | 5/1980 | European Pat. Off. |
| 0109703 | 11/1983 | European Pat. Off. |
| 0146165 | 11/1984 | European Pat. Off. |
| A152314 | 8/1985 | European Pat. Off. |
| 0152314 | 9/1985 | European Pat. Off. |
| 0175558 | 3/1986 | European Pat. Off. |
| 2613226 | 9/1977 | Fed. Rep. of Germany |
| 3318855 | 11/1984 | Fed. Rep. of Germany |
| 3717111A | 11/1987 | Fed. Rep. of Germany |
| 62-53740 | 3/1987 | Japan |
| 80879 | 2/1983 | Romania |
| 1436773 | 5/1976 | United Kingdom |
| 1600517 | 10/1981 | United Kingdom |

*Primary Examiner*—Joseph E. Evans

[57] ABSTRACT

In one embodiment, the invention relates to a catalyst in powdered form which comprises a major amount of the oxides of copper and zinc, and a minor amount of aluminum oxide wherein the pore volume of pores of said catalysts having a diameter between about 120 and about 1000 Å is at least about 40% of the total pore volume. In another embodiment, the invention relates to a process for preparing hydrogenation catalysts comprising the oxides of copper, zinc and aluminum which comprises the steps of (A) preparing a first aqueous solution containing at least one water-soluble copper salt and at least one water-soluble zinc salt;

(B) preparing a second solution containing at least one water-soluble basic aluminum salt and at least one alkaline precipitating agent;

(C) mixing the first and second solutions whereby an insoluble solid is formed;

(D) recovering the insoluble solid.

The invention also relates to a process for hydrogenating aldehydes, ketones, carboxylic acids and carboxylic acid esters with catalysts of the type described. Catalysts of the invention are useful in both fixed bed and slurry phase hydrogenation reactions.

19 Claims, 2 Drawing Sheets

U.S. PATENT DOCUMENTS

| | | | |
|---|---|---|---|
| 3,546,140 | 12/1970 | Gutmann et al. | 252/466 |
| 3,729,520 | 4/1973 | Rutzen et al. | 260/638 A |
| 3,894,054 | 7/1975 | Miya | 260/346.1 |
| 3,907,715 | 9/1975 | Arai et al. | 252/465 |
| 3,927,120 | 12/1975 | Grane et al. | 502/343 |
| 3,927,121 | 12/1975 | Grane et al. | 260/618 H |
| 3,961,037 | 6/1976 | Davies et al. | 423/656 |
| 3,971,735 | 7/1976 | Asane et al. | 252/432 |
| 3,988,263 | 10/1976 | Hansford | 252/466 J |
| 4,048,196 | 9/1977 | Broecker et al. | 260/346.11 |
| 4,092,269 | 5/1978 | Mount et al. | 502/209 |
| 4,111,847 | 9/1978 | Stiles | 252/463 |
| 4,113,662 | 9/1978 | Wall | 252/473 |
| 4,181,810 | 1/1980 | Immel et al. | 568/807 |
| 4,279,781 | 7/1981 | Dienes et al. | 252/463 |
| 4,291,126 | 9/1981 | Sugier et al. | 518/713 |
| 4,376,721 | 3/1983 | Huang | 252/430 |
| 4,386,018 | 5/1983 | Merger et al. | 252/465 |
| 4,386,219 | 5/1983 | Merger et al. | 568/853 |
| 4,393,251 | 7/1983 | Broecker et al. | 568/811 |
| 4,405,819 | 9/1983 | Duckwall, Jr. | 568/814 |
| 4,421,939 | 12/1983 | Kiff et al. | 568/885 |
| 4,436,833 | 3/1984 | Broecker et al. | 502/176 |
| 4,440,668 | 4/1984 | Cheng et al. | 502/331 |
| 4,513,100 | 4/1985 | Fattore et al. | 502/303 |
| 4,535,071 | 8/1985 | Schneider et al. | 502/342 |
| 4,551,444 | 11/1985 | Lin et al. | 502/313 |
| 4,588,848 | 5/1986 | Butter et al. | 568/885 |
| 4,596,782 | 6/1986 | Courty et al. | 502/302 |
| 4,632,916 | 12/1986 | Bither, Jr. | 502/209 |
| 4,675,343 | 6/1987 | Courty et al. | 518/713 |
| 4,677,234 | 6/1987 | Bartley | 568/864 |
| 4,704,480 | 11/1987 | Gefri et al. | 568/396 |
| 4,804,790 | 2/1989 | Schaett | 568/885 |
| 4,808,562 | 2/1989 | Kubersky et al. | 502/172 |
| 4,851,593 | 7/1989 | Gilbert | 568/864 |
| 4,863,894 | 9/1989 | Chinchen et al. | 502/342 |
| 4,871,710 | 10/1989 | Denny et al. | 502/414 |
| 5,004,845 | 4/1991 | Bradley et al. | 568/885 |

FIG. 1

HYDROGENATION CATALYST, PROCESS FOR PREPARING AND PROCESS OF USING SAID CATALYST

CROSS REFERENCE TO RELATED APPLICATION

This application is a division of application Ser. No. 07/680,100 filed Apr. 2, 1991, now U.S. Pat. No. 5,155,086 which in turn is a continuation-in-part of application Ser. No. 07/422,624 filed Oct. 17, 1989 now abandoned which in turn is a continuation-in-part of application Ser. No. 07/405,983 filed Sep. 12, 1989 now abandoned.

TECHNICAL FIELD

This invention relates to catalysts which are particularly useful as hydrogenation catalysts, and more particularly, as catalysts for hydrogenating aldehydes, ketones, carboxylic acids and carboxylic esters. The invention also relates to a method of preparing said catalysts and to the use of the catalysts in hydrogenation reactions.

BACKGROUND OF THE INVENTION

In one embodiment, the present invention relates to catalysts which are useful in hydrogenation reactions and which comprise the oxides of copper, zinc and aluminum. The preparation of various copper-containing catalysts and the use of such catalysts in various reactions has been described previously. Such reactions include hydrogenation reactions, the synthesis of methanol and higher alcohols from synthesis gas, etc. The copper-containing catalysts also may contain other metal oxides including chromium oxide, zinc oxide, titanium oxide, zirconium oxide, iron oxide, alumina, silica, etc., and mixtures of one or more of said oxides.

The hydrogenation of carboxylic acids and carboxylic esters to alcohols is known in the art, and various methods and catalysts have been suggested for effecting the hydrogenation reaction. For example, the ester may be reduced with lithium aluminum hydride or sodium and alcohol. A commonly practiced method involves the use of a copper-chromite-based hydrogenation catalyst. While copper chromite catalysts are commercially available and successful, the disposal of the spent copper chromite catalyst is a problem since chromium is present in the spent catalyst, and chromium is a highly toxic material which is subject to stringent EPA disposal regulations. Because of the stringent regulations, the cost of the manufacture, use and disposal of copper chromite catalysts has increased. It is anticipated that in the future, more stringent EPA regulations and escalating disposal costs will adversely affect the economics of using a copper-chromite-based catalyst.

U.S. Pat. No. 2,091,800 describes a copper chromite/barium catalyst which is used in a process for hydrogenating esters at a temperature in the range of 200° C. to 400° C. by passing the acid and its esters over the hydrogenation catalyst. Other patents describing various types of copper chromite catalysts used in acid and ester hydrogenation processes include U.S. Pat. Nos. 2,121,367; 2,782,243; 3,173,959; and 3,267,157.

U.S. Pat. No. 3,894,054 describes the production of tetrahydrofuran by catalytic hydrogenation and dehydration of maleic anhydride using a catalyst composition which comprises a mixture obtained by calcining a silica-alumina catalyst and a copper-chromium-zinc catalyst. U.S. Pat. No. 3,971,735 describes the preparation of methanol from syngas with a catalyst comprised of copper, zinc, aluminum and boron. The hydrogenation of esters to alcohols by contacting the ester with hydrogen and a catalyst comprising cobalt, zinc and copper under catalytic hydrogenation conditions is described in U.S. Pat. No. 4,113,662. U.S. Pat. No. 4,279,781 describes a methanol synthesis catalyst which comprises the oxides of copper and zinc and a minor amount of a thermal stabilizing metal oxide such as alumina. The copper to zinc metal-weight ratio is in the range of from 2:1 to 3.5:1. Catalysts comprising copper, cobalt, a metal selected from chromium, iron, vanadium or manganese, a rare earth metal and a small amount of an alkali or alkaline earth metal are described in U.S. Pat. No. 4,291,126. Optionally, the catalyst may contain zinc and/or a noble metal and/or a binder selected from alumina, magnesia and cements. U.S. Pat. No. 4,440,668 describes a three-component oxide catalyst based on copper, a metal from Group VIA, VIIA or VIIIA, and a metal of Group IVA or VA. The preferred catalyst is based on copper, cobalt and zirconium with the first two components being formed by co-precipitation in the presence of the oxide of the third component. Another multi-component catalytic system is described in U.S. Pat. No. 4,513,100 which comprises zinc, chromium, copper, one or more alkaline metals and possibly one or more metals chosen from molybdenum, manganese, lanthanum, cerium, aluminum, titanium and vanadium.

U.S. Pat. No. 4,535,071 describes a catalyst for methanol synthesis from syngas which comprises as catalytically active substances, copper oxide and zinc oxide and as a thermal stabilizing substance, aluminum oxide. Optimum yields of methanol are obtained when the atomic ratio of copper to zinc is between 2.8 and 3.8. Five-component catalyst compositions are described in U.S. Pat. No. 4,551,444 and the essential components are copper, an iron group component, a component of elements 23-26, an alkaline metal compound and a precious metal compound. Catalysts comprising copper oxide and zinc oxide in a ratio of 8:1 to 1:1 are described in U.S. Pat. No. 4,588,848 as being useful in synthesizing neoalcohols from neoacids. U.S. Pat. No. 4,598,061 describes a catalyst for synthesis of methanol and alcohol mixtures from synthesis gas using a catalyst which contains, as an oxide precursor, copper oxide and zinc oxide; aluminum oxide as a thermal stabilizing substance; and at least one alkali metal compound. Catalysts comprising copper and cobalt, and optionally aluminum and/or zinc and/or sodium are utilized in U.S. Pat. No. 4,675,343 for preparing primary aliphatic alcohols from hydrogen and carbon oxides. The catalysts contain a minimum of 3% cobalt. Catalysts containing the oxides of copper, zinc and alumina are described in U.S. Pat. No. 4,704,480 as being useful in the production of aliphatic ketones and an optional consecutive production of the corresponding carbinols. More specifically, catalysts comprising the oxides of copper, zinc and alumina are utilized in Examples 1 and 11 of the patent and a catalyst comprising the oxides of copper and alumina is utilized in Example 12. Copper-zinc catalysts also are described in U.S. Pat. No. 4,808,562, and the catalysts may contain alumina.

U.K. Pat. No. 1,436,773 also describes copper oxide, zinc oxide catalysts obtained by coprecipitation which are suitable for use in the synthesis of methanol from synthesis gas. The ratio of copper to zinc in the catalyst is from 1:1 to 8:1, and the catalyst may contain a thermal stabilizer such as alumina. Japanese Patent 62-53740 apparently describes catalysts derived from the nitrates of copper, zinc, manganese/magnesium and aluminum.

German Offenlegungschrift 2,613,226 describes a continuous preparation of fatty alcohols by catalytic hydrogenation of relatively high molecular weight fatty acids and esters formed with low-molecular weight monohydric alcohols. The process utilizes hydrogen and a catalyst. The catalysts disclosed in the patent include copper chromite or copper-zinc-chromite and copper-zinc catalysts with or without known carrier substances.

Although many copper-containing catalysts have been described in the prior art, there continues to be a need for catalysts which are useful particularly in the hydrogenation of aldehydes, acids and esters, including diesters. It is also desirable to prepare catalysts useful in hydrogenation reactions which can be carried out in either a fixed bed or a fluidized bed reactor.

SUMMARY OF THE INVENTION

In one embodiment, the invention relates to a catalyst in powdered form which comprises a major amount of the oxides of copper and zinc, and a minor amount of aluminum oxide wherein the pore volume of pores of said catalyst having a diameter of between about 120 and 1000 Å is at least about 40% of the total pore volume. In another embodiment, the invention relates to a process for preparing hydrogenation catalysts comprising the oxides of copper, zinc and aluminum which comprises the steps of (A) preparing a first aqueous solution containing at least one water-soluble copper salt and at least one water-soluble zinc salt;

(B) preparing a second solution containing at least one water-soluble basic aluminum salt and at least one alkaline precipitating agent;

(C) mixing the first and second solutions whereby an insoluble solid is formed;

(D) recovering the insoluble solid.

The invention also relates to a process for hydrogenating aldehydes, ketones, carboxylic acids and carboxylic acid esters with catalysts of the type described. Catalysts of the invention are useful in both fixed bed and slurry phase hydrogenation reactions.

DESCRIPTION OF THE PREFERRED EMBODIMENTS

In one embodiment, the present invention relates to a catalyst in powder form comprising a major amount of the oxides of copper and zinc and a minor amount of aluminum oxide wherein the pore volume of pores of said powders having a diameter of between about 120 and 1000 Å is at least about 40% of the total pore volume. In one preferred embodiment, the pore volume of pores having a diameter of greater than 120 Å is at least about 70% of the total pore volume. All references to pore diameters and pore volumes in the specification and claims are based upon measurements utilizing mercury porosimetry. A typical method is described by R. Anderson, *Experimental Methods in Catalytic Research*, Academic Press, New York, 1968. The pore volumes are determined utilizing the powder forms of the catalysts in their oxide forms. That is, the pore diameters reported herein are obtained for the powder catalyst after calcination, but prior to any reduction of the oxide, and the pore volumes are given as a percentage of the total pore volume contained in pores up to about 1000 Å. Those skilled in the art often refer to the catalyst containing the metal oxides as the "oxide" or "oxidic precursor" form of the catalyst.

The powdered catalysts of the present invention which contain a major amount of the oxides of copper and zinc, and a minor amount of aluminum oxide, also may be characterized as having an average surface area of at least about 50 square meters per gram and more generally from about 50 to about 200 square meters per gram. The powdered catalysts also may be characterized as having an average particle diameter of from about 8 to about 30 microns.

In another embodiment, the catalysts of the present invention may be characterized as having a copper to zinc atomic ratio of from about 0.2 to about 5.5, or from about 0.5 to about 3.0. In other embodiments, the atomic ratio of copper to zinc may be less than about 1.

In a further embodiment, the present invention relates to a catalyst comprising the oxides of copper, zinc and aluminum wherein the atomic ratio of copper to zinc is less than about 0.85 and provided that the catalyst does not contain chromium, boron or cobalt. More particularly, the atomic ratio of copper to zinc is from about 0.5 to about 0.85.

The amount of aluminum oxide contained in the catalyst of this invention may be varied over a wide range although the catalyst will generally contain from about 3% to about 50% by weight of aluminum oxide, and more often contains from about 18% to about 30% by weight of aluminum oxide. The catalyst of the invention also may be characterized by an atomic ratio of copper and zinc to aluminum of less than about 15.

The catalysts of the present invention can be generally obtained by precipitating the copper, zinc and aluminum components by addition of an aqueous alkaline solution.

One embodiment of the present invention relates to a preferred process for preparing a hydrogenation catalyst comprising the oxides of copper, zinc and aluminum, and the process comprises the steps of (A) preparing a first aqueous solution containing at least one water-soluble copper salt and at least one water-soluble zinc salt;

(B) preparing a second solution containing at least one water-soluble basic aluminum salt and at least one alkaline precipitating agent;

(C) mixing the first and second solutions whereby an insoluble solid is formed;

(D) recovering the insoluble solid; and (E) calcining the recovered solid.

The catalyst prepared in accordance with the above method may be characterized as having an atomic ratio of copper to zinc of from about 0.2 to about 5.5. Such catalysts are prepared by maintaining the atomic ratio of copper to zinc in the first aqueous solution within the indicated range. In another embodiment, the atomic ratio of copper to zinc in the first aqueous solution is from about 0.5 to about 3.0, and in other embodiments the ratio may be less than about 1, or less than about 0.85. The amount of alumina contained in the catalyst recovered from the calcination of the removed solid in step (E) may contain from about 3% to about 50% by weight of aluminum oxide, and more generally, from about 18% to about 30% by weight of aluminum oxide.

The first and second solutions described above may be mixed in any manner or order. Thus, the first solution can be added to the second solution, or the second solution can be added to the first solution, or a mixture of the two solutions can be obtained by simultaneously mixing the two solutions such as by simultaneously adding the two solutions to a vessel. It is desirable that the mixing of the first and second solutions in step (C) be conducted at a pH above about 5.5, and more generally above about 7.0. When the two solutions are mixed simultaneously, the pH of the resulting mixture can be controlled by varying the rate of addition of the second solution which contains an alkaline material. As the rate of addition of the second solution increases, the pH of the resulting mixture increases.

The water-soluble copper and zinc salts utilized to form the first solution are copper and zinc salts such as the nitrates, acetates, sulfates, chlorides, etc. It is presently preferred, however, to use the nitrates of copper and zinc in the formation of the first solution. Any water-soluble aluminum salt can be utilized to prepare the second solution, and the aluminum salt generally is a basic aluminum salt such as sodium aluminate.

The second solution also contains at least one alkaline material which may be a soluble base such as sodium hydroxide, sodium carbonate, ammonium hydroxide, ammonium carbonate, etc., and mixtures thereof. The amount of alkaline material included in the second solution may be varied over a wide range, and the amount of alkaline materials should be sufficient to provide an alkaline solution which, when added to the first solution will result in a mixture having the desired pH. The pH of the mixture obtained by mixing the first and second solutions should be within the range of from about 5.5 to about 9.0 and more preferably is at least 7, and most preferably at least about 7.5. As noted above, the pH of the mixture can be maintained as desired by adjusting the relative addition rates of the two solutions. Additionally, the mixture obtained from the first and second solutions should be maintained at a temperature of from about 50°-95° C. A precipitate is formed and recovered by techniques well known in the art such as by filtration, centrifugation, etc. The recovered precipitate preferably is washed with water to remove impurities, dried by heating to a temperature of up to about 150° C., and finally calcined. The recovered precipitate is calcined at a temperature in the range of from about 475° C. to about 700° C. for a period of about 30 to about 120 minutes. Generally, calcination at a temperature of about 500° C. for about 30 minutes is sufficient.

The catalysts which are obtained by the above-described co-precipitation procedure generally are characterized as having an average particle size of from about 8 to about 30 microns, and the particles have an average surface area of at least about 50 square meters per gram. In one embodiment, the surface area will range from about 70 to about 200 square meters per gram. The pore volume of pores in said catalysts having a diameter of between about 120 and 1000 Å is often at least about 40% of the total pore volume, and more often, more than 70% of the total pore volume.

In addition to having small particle sizes, the catalysts of the present invention are also characterized by a narrow Malvern particle size distribution. A narrow particle size distribution can also be observed with a scanning electron microscope at magnifications such as 500 and 1000.

The products of the present invention, prior to calcination are also characterized by X-ray diffraction patterns (PXRD) indicating the presence of one or more of the following phrases; (1) $[Cu_{(6-x)}Zn_x]Al_2(OH)_{16}CO_3.4H_2O$; (2) $[Cu_{(2-x)}Zn_x]CO_3(OH)_2$; (3) $Zn_4CO_3(OH)_6H_2O$; (4) $Zn_5(CO_3)_2(OH)_6$; and (5) $Cu_{0.4}Zn_{1.85}Al_{0.75}O_5$. In one embodiment, phase 1 is a preferred phase. PXRD also indicates the amount of crystallinity present in the products. The products are generally characterized as having relatively high crystallinity, and in one embodiment wherein the aluminum content of the product is from about 12 to 20% or higher, the average crystal size for the major phase present is in the range of from about 80 to about 1000 Å and more often from about 280 to about 1000 Å.

The following examples illustrate the above-described preferred embodiments for preparing the hydrogenation catalyst of the present invention. Unless otherwise indicated in the examples and elsewhere in the specification and claims, all parts and percentages are by weight, temperatures are in degrees Centigrade, and pressures are at or near atmospheric.

EXAMPLE 1

A first solution is prepared from 500 parts of an aqueous copper nitrate solution containing 16.3% copper, 625 parts of an aqueous zinc nitrate solution containing 16.5% zinc and 1000 parts of water. A second solution is prepared from 321 parts of an aqueous sodium aluminate solution (containing about 10% aluminum) and 304 parts soda ash and 1000 parts water. The two solutions are mixed in a reaction vessel that contains 3000 parts water at 95° C. The reaction temperature is maintained at 95° C. ($\pm$5° C.) and the pH is maintained at about 7.5. A precipitate is formed and recovered by filtration. The recovered precipitate is washed with water, dried at 125° C. and finally calcined at 600° C. ($\pm$10° C.) for 45 minutes. The physical and chemical characteristics of the calcined product are given in Table I.

EXAMPLE 2

A first solution is prepared from 467 parts of an aqueous copper nitrate solution containing 16.3% copper, 933 parts of an aqueous zinc nitrate solution containing 16.5% zinc and 200 parts water. A second solution is prepared by dissolving 35 parts sodium aluminate (23% Al), 126 parts of an aqueous solution of sodium hydroxide (50% NaOH) and 413 parts soda ash in 1200 parts water. The two solutions are mixed in a reaction vessel that contains 5000 parts water at 70° C. The reaction temperature is maintained at 70° C. ($\pm$5° C.), and the pH is maintained at about 7.5. A precipitate is formed and recovered by filtration. It is then washed with water, dried at 125° C. and finally calcined at 500° C. ($\pm$10° C.) for 30 minutes. The physical and chemical characteristics of the calcined product are given in Table I.

EXAMPLE 3

A first solution is prepared from 351 parts of an aqueous copper nitrate solution containing 16.3% copper, 1050 parts of an aqueous zinc nitrate solution containing 16.5% zinc and 220 parts water. A second solution is prepared by dissolving 35 parts sodium aluminate (23% Al), 126 parts of an aqueous solution of sodium hydroxide (50% NaOH) and 413 parts soda ash in 1200 parts water. The two solutions are mixed in a reaction vessel that contains 5000 parts water at 70° C. The reaction temperature is maintained at 70° C. (±5° C.), and the pH is maintained at about 7.5. A precipitate is formed and recovered by filtration. It is then washed with water, dried at 125° C. and calcined at 500° C. for 30 minutes. The physical and chemical characteristics of the calcined product are given in Table I.

EXAMPLE 4

A first solution is prepared from 622 parts of an aqueous copper nitrate solution containing 16.3% copper, 778 parts of an aqueous zinc nitrate solution containing 16.5% zinc and 200 parts water. A second solution is prepared by dissolving 35 parts sodium aluminate (23% Al), 86 parts of an aqueous solution of sodium hydroxide (50% NaOH) and 413 parts soda ash in 1237 parts water. The two solutions are mixed in a reaction vessel that contains 5000 parts water at 70° C., and the pH is maintained at about 7.5. A precipitate is formed and recovered by filtration. It is then washed with water, dried at 125° C. and calcined at 500° C. for 30 minutes. The physical and chemical characteristics of the calcined product are given in Table I.

EXAMPLE 5

A first solution is prepared from 710 parts of an aqueous copper nitrate solution containing 16.5% zinc and 1452 aqueous zinc nitrate solution containing 16.5% zinc and 1452 parts water. A second solution is prepared by dissolving 330 parts sodium aluminate (23% Al), 30 parts of an aqueous solution of sodium hydroxide (50% NaOH) and 350 parts soda ash in 2252 parts water. The two solutions are mixed in a reaction vessel that contains 5000 parts water at 70° C. The reaction temperature is maintained at 70° C., and the pH is maintained at about 7.5. A precipitate is formed and recovered by filtration. It is then washed with water, dried at 125° C. and calcined at 500° C. for 30 minutes. The physical and chemical characteristics of the calcined product are given in Table I.

EXAMPLE 6

A first solution is prepared from 324 parts of an aqueous copper nitrate solution containing 16.3% copper, 1291 parts of an aqueous zinc nitrate solution containing 16.5% zinc and 1489 parts water. A second solution is prepared by dissolving 330 parts sodium aluminate (23% Al), 10 parts of an aqueous solution of sodium hydroxide (50% NaOH) and 350 parts soda ash in 2212 parts water. The two solutions are mixed in a reaction vessel that contains 5000 parts water at 70° C., and the pH is maintained at about 7.5. A precipitate is formed and recovered by filtration. It is then washed with water, dried at 125° C. and calcined at 600° C. for 45 minutes. The physical and chemical characteristics of the calcined product are given in Table I.

EXAMPLE 7

A first solution is prepared from 710 parts of an aqueous copper nitrate solution containing 16.3% copper, 899 parts of an aqueous zinc nitrate solution containing 16.5% zinc and 1414 parts water. A second solution is prepared by mixing 286 parts of aqueous solution of sodium aluminate (13% Al), 21 parts of an aqueous solution of sodium hydroxide (50% NaOH) and 350 parts soda ash in 1100 parts water. The two solutions are mixed in a reaction vessel that contains 5000 parts water at 70° C. The reaction temperature is maintained at 70° C., and the pH is maintained at about 7.5. A precipitate is formed and recovered by filtration. It is then washed with water, dried at 125° C. and calcined at 600° C. for 45 minutes. The physical and chemical characteristics of the calcined product are given in Table IA.

EXAMPLE 8

A first solution is prepared from 1000 parts of an aqueous nitrate solution containing 16.3% copper, 335 parts of an aqueous zinc nitrate solution containing 16.5% zinc and 1600 parts water. A second solution is prepared by dissolving 113 parts sodium aluminate (23% Al) and 490 parts soda ash in 2500 parts water. The two solutions are mixed in a reaction vessel that contains 5000 parts water at 70° C. The reaction temperature is maintained at 70° C. (±5° C.), and the pH of the mixture is maintained at 7.5. A precipitate is formed and recovered by filtration. It is then washed with water, dried at 125° C. and finally calcined at 500° C. (±10° C.) for 75 minutes. The physical and chemical characteristics of the calcined product are shown in Table IA.

EXAMPLE 9

A first solution is prepared from 1000 parts of an aqueous copper nitrate solution containing 16.4% copper, 253 parts of an aqueous zinc nitrate solution containing 16.5% zinc and 1600 parts water. A second solution is prepared by dissolving 37 parts sodium aluminate (23% Al) and 450 parts soda ash in 2300 parts water. The two solutions are mixed in a reaction vessel that contains 5000 parts water at 70° C. The reaction temperature is maintained at 70° C. (±5° C.), and the pH of the mixture is maintained at about 7.5. A precipitate is formed and recovered by filtration. It is then washed with water, dried at 125° C. and finally calcined at 480° C. (±10° C.) for 50 minutes. The physical and chemical characteristics of the calcined product are shown in Table IA.

EXAMPLE 10

A first solution is prepared from 1000 parts of an aqueous copper nitrate solution containing 16.3% copper, 200 parts of an aqueous zinc nitrate solution containing 16.5% zinc and 200 parts water. A second solution is prepared by dissolving 35 parts sodium aluminate (23% Al), 126 parts of an aqueous sodium hydroxide solution (50% NaOH), and 413 parts soda ash in 1000 parts water. The two solutions are mixed in a reaction vessel that contains 5000 parts water at 70° C. The reaction temperature is maintained at 70° C. (±5° C.), and the pH of the mixture is maintained at about 7.5. A precipitate is formed and recovered by filtration. It is then washed with water, dried at 125° C. and finally calcined at 500° C. (±10° C.) for 30 minutes. The physical and chemical characteristics of the calcined product are shown in Table IA.

TABLE I

| | Example | | | | | |
|---|---|---|---|---|---|---|
| | 1 | 2 | 3 | 4 | 5 | 6 |
| Cu/Zn Molar Ratio | 0.77 | 0.52 | 0.36 | 0.84 | 0.81 | 0.26 |
| (Cu + Zn)/Al Ratio | 2.36 | 12.3 | 8.79 | 11.89 | 2.06 | 1.75 |
| Surf. Area (M$^2$/g) | 92 | 90.9 | 89.1 | 85.3 | 143 | 179 |
| He Density (g/cc) | 4.39 | 5.16 | 4.62 | 4.77 | 3.96 | 4.37 |
| Hg Density @ 18.5 PSI | 0.44 | 0.50 | 0.50 | 0.49 | 0.49 | 0.47 |
| Hg Pore Volume (cc/g)* | | | | | | |
| Pore Diameter (Å) | | | | | | |
| Up to 60 | 26.19 | 13.04 | 16.67 | 0.00 | 24.00 | 7.25 |
| Up to 80 | 33.33 | 17.39 | 20.37 | 0.00 | 28.00 | 23.19 |
| Up to 100 | 38.10 | 21.74 | 25.93 | 0.00 | 32.00 | 43.48 |
| Up to 120 | 40.48 | 28.26 | 31.48 | 0.00 | 36.00 | 55.07 |
| Up to 350 | 69.05 | 76.09 | 68.52 | 68.63 | 66.00 | 88.41 |
| Up to 700 | 88.10 | 93.48 | 90.74 | 92.16 | 88.00 | 97.10 |
| Up to 1000 | 100 | 100 | 100 | 100 | 100 | 100 |
| Median Particle | | | | | | |
| Size (μm) | 14.0 | 15.8 | 15.2 | 15.1 | 18.7 | 17.1 |
| Size Span (90%–10%) | 11.3 | 20.3 | 19.9 | 20.5 | 19.5 | 19.9 |
| Chemical Analysis | | | | | | |
| at 500° C. (% wt.) | | | | | | |
| Copper | 25.9 | 24.8 | 18.2 | 33.3 | 22.93 | 10.96 |
| Zinc | 34.0 | 48.8 | 51.5 | 40.6 | 29.00 | 43.90 |
| Aluminum | 10.7 | 2.50 | 3.30 | 2.60 | 14.40 | 13.05 |
| Sodium | 0.10 | 0.04 | 0.07 | 0.08 | 0.04 | 0.13 |

*Cumulative percentage.

TABLE IA

| | Example | | | |
|---|---|---|---|---|
| | 7 | 8 | 9 | 10 |
| Cu/Zn Molar Ratio | 0.82 | 1.94 | 4.08 | 5.16 |
| (Cu + Zn)/Al Ratio | 2.29 | 2.07 | 10.4 | 12.3 |
| Surf. Area (M$^2$/g) | 120 | 79.9 | 70.1 | 69.0 |
| He Density (g/cc) | 4.39 | 4.92 | 5.10 | 5.20 |
| Hg Density @ 18.5 PSI | 0.41 | 0.51 | 0.65 | 0.78 |
| Hg Pore Volume (cc/g)* | | | | |
| Pore Diameter (Å) | | | | |
| Up to 60 | 16.67 | 2.08 | 13.21 | 6.56 |
| Up to 80 | 23.33 | 4.17 | 13.21 | 8.20 |
| Up to 100 | 30.00 | 4.17 | 16.98 | 8.20 |
| Up to 120 | 36.67 | 6.25 | 20.75 | 9.84 |
| Up to 350 | 63.33 | 39.58 | 66.04 | 57.38 |
| Up to 700 | 83.33 | 75.00 | 86.68 | 88.52 |
| Up to 1000 | 100 | 100 | 100 | 100 |
| Median Particle | | | | |
| Size (μm) | 17.4 | 23 | 22.3 | 16.9 |
| Size Span (90%–10%) | 13.1 | 33.3 | 24.7 | 51.7 |
| Chemical Analysis | | | | |
| at 500° C. (% wt.) | | | | |
| Copper | 25.6 | 44.5 | 58.7 | 61.9 |
| Zinc | 32.00 | 23.6 | 14.8 | 12.2 |
| Aluminum | 10.54 | 2.96 | 7.1 | 15.2 |
| Sodium | 0.10 | 0.30 | 0.11 | 0.07 |

*Cumulative percentage.

The following examples C-1 to C-7 illustrate the preparation of control catalysts which are not within the present invention but are presented herein for comparison purposes.

EXAMPLE C-1

Cu/Zn

A first solution is prepared from 1000 parts of an aqueous copper nitrate solution containing 16.3% copper, 1017 parts of an aqueous zinc nitrate solution containing 16.5% zinc and 689 parts water. A second solution is prepared from 374 parts of soda ash in 1012 parts water. The two solutions are mixed in a reaction vessel that contains 2000 parts water at 45° C. The pH is maintained at about 7.5, and a precipitate is formed and recovered by filtration. It is then washed with water, dried at 125° C. and calcined at 500° C. for 30 minutes. The physical and chemical characteristics of the calcined product are given in Table IB.

EXAMPLE C-2

Cu/Al

A first solution is prepared from 1010 parts of an aqueous copper nitrate solution containing 16.3% copper and 1640 parts water. A second solution is prepared from 374 parts of soda ash in 1012 parts water. The two solutions are mixed in a reaction vessel that contains 2000 parts water at 45° C. The pH is maintained at about 7.5, and a precipitate is formed and recovered by filtration. It is then washed with water, dried at 125° C. and calcined at 500° C. for 30 minutes. The physical and chemical characteristics of the calcined product are given in Table IB.

EXAMPLE C-3

Zn/Al

A first solution is prepared from 1015 parts of an aqueous zinc nitrate solution containing 16.5% zinc and 1745 parts water. A second solution is prepared by dissolving 342 parts sodium aluminate (23% Al) and 250 parts soda ash in 2210 parts water. The two solutions are mixed in a reaction vessel that contains 5000 parts water at 70° C. The reaction temperature is maintained at 70° C. and the pH is maintained at about 7.5. A precipitate is formed and recovered by filtration. It is then washed with water, dried at 125° C. and calcined at 500° C. for 30 minutes. The physical and chemical characteristics of the calcined product are given in Table IB.

EXAMPLE C-4

Cu/Zn/Al/Co

A first solution is prepared from 500 parts of an aqueous copper nitrate solution containing 16.3% copper, 254 parts of an aqueous zinc nitrate solution containing 16.5% zinc, and 17 parts of cobalt nitrate hexahydrate. A second solution is prepared by mixing 115 parts of sodium aluminate (23% Al) and 250 parts soda ash in 2485 parts water. The two solutions are mixed in a reaction vessel that contains 2140 parts water at 70° C. The reaction temperature is maintained at about 70° C., and the pH is maintained at about 7.5. A precipitate is formed and recovered by filtration. It is then washed with water, dried at 125° C. and calcined at 500° C. for 30 minutes. The physical and chemical characteristics of the calcined product are given in Table IB.

EXAMPLE C-5

Cu/Zn/Co

A first solution is prepared from 501 parts of an aqueous copper nitrate solution containing 16.3% copper, 255 parts of an aqueous zinc nitrate solution containing 16.5% zinc, and 34 parts of cobalt nitrate hexahydrate. A second solution is prepared from 365 parts soda ash in 2487 parts water. The two solutions are mixed in a reaction vessel that contains 2140 parts water at 70° C. The reaction temperature is maintained at about 70° C., and the pH is maintained at about 7.5. A precipitate is formed and recovered by filtration. It is then washed with water, dried at 125° C. and calcined at 500° C. for 30 minutes. The physical and chemical characteristics of the calcined product are given in Table IB.

EXAMPLE C-6

Cu/Cr/Mn

A first solution made up of 600 parts of a copper nitrate solution (16.3% Cu), 31.5 parts of a manganese nitrate solution (15.5% Mn) and 175 parts chromic acid ($CrO_3$) and a second solution made up of 362 parts concentrated ammonium hydroxide and 132 parts water are added to a reaction vessel, containing 1500 parts water at 50° C., to form a precipitate. The precipitate is collected by filtration and washed with water. After drying at 150° C. for 12 hours, the material is calcined at 420° C. for 30 minutes. The physical and chemical characteristics of the calcined product are given in Table IB.

EXAMPLE C-7

A first solution is prepared from 701 parts of an aqueous copper nitrate solution containing 16.3% copper, 702 parts of an aqueous zinc nitrate solution containing 16.5% zinc and 208 parts water. A second solution is prepared by dissolving 415 parts soda ash in 1000 parts water. The two solutions are mixed in a reaction vessel that contains 5000 parts water in which 100 parts of a hydrated alumina powder (Kaiser Versal/850) is dispersed. The reaction temperature is maintained at 70° C. (±5° C.), and the pH is maintained at about 7.5. A precipitate is formed and recovered by filtration. It is then washed with water, dried at 125° C. and calcined at 500° C. (±10° C.) for 30 minutes. The physical and chemical characteristics of the calcined product are given in Table IB.

TABLE IB

|  | Example | | | | | | |
|---|---|---|---|---|---|---|---|
|  | C-1 | C-2 | C-3 | C-4 | C-5 | C-6 | C-7 |
| Cu/Zn Molar Ratio | 1.01 | 1011 | 0.00 | 2.11 | 2.14 | — | 1.07 |
| (Cu + Zn)/Al Ratio | — | 1.25 | 0.69 | 2.28 | — | — | 2.33 |
| Surf. Area ($M^2/g$) | 16.6 | 82.4 | 158 | 98.3 | — | 60 | 48.9 |
| He Density (g/cc) | 5.06 | 3.56 | 4.09 | 4.01 | 5.81 | 4.9 | 4.00 |
| Hg Density @ 18.5 PSI | 1.08 | 0.47 | 0.46 | 0.38 | 1.21 | 1.6 | 1.17 |
| Hg Pore Volume (cc/g)* | | | | | | | |
| Pore Diameter (Å) | | | | | | | |
| Up to 60 | 12.90 | 0.00 | 4.00 | 10.87 | 14.29 | — | 17.39 |
| Up to 80 | 12.90 | 1.67 | 14.00 | 10.87 | 14.29 | — | 19.57 |
| Up to 100 | 12.90 | 3.33 | 18.00 | 10.87 | 14.29 | — | 21.74 |
| Up to 120 | 12.90 | 5.00 | 52.00 | 10.87 | 14.29 | — | 23.91 |
| Up to 350 | 16.13 | 41.67 | 78.00 | 36.96 | 62.86 | — | 69.57 |
| Up to 700 | 74.19 | 78.33 | 92.00 | 76.09 | 88.57 | — | 95.65 |
| Up to 1000 | 100 | 100 | 100 | 100 | 100 | — | 100 |
| Median Particle | | | | | | | |
| Size (μm) | 19.5 | 17.2 | 18.3 | 22.3 | 12.6 | 22 | 57.5 |
| Size Span (90%–10%) | 77.2 | 22.1 | 19.6 | 31.5 | 44.5 | — | 80.7 |
| Chemical Analysis | | | | | | | |
| at 500° C. (% wt.) | | | | | | | |
| Copper | 34.5 | 49.1 | 0.00 | 39.2 | 51.0 | 35.7 | 28.1 |
| Zinc | 35.0 | 0.05 | 29.4 | 19.1 | 24.6 | Cr = 31.7 | 27.0 |
| Aluminum | — | 16.7 | 17.6 | 11.4 | — | — | 9.90 |
| Sodium | 4.10 | 1.04 | 0.04 | 0.19 | 0.09 | — | 5.40 |
| Other | — | — | — | Co = 3.1 | Co = 4.2 | Mn = 3.7 | — |

*Cumulative percentage.

Examples 11–14, described below, are additional examples of the process and catalysts of the invention. Examples C-8 to C-11 are comparative examples wherein the procedures used in Examples 11–14, respectively, are modified to represent prior art procedures.

EXAMPLE 11

A first solution is prepared from 371 parts of an aqueous solution of copper nitrate containing 16.3% copper, 754 parts of an aqueous zinc nitrate solution containing 16.5% zinc and 1013 parts water. A second solution is prepared from 428 parts soda ash, 177 parts of an aqueous sodium aluminate solution (containing about 10% aluminum) and 1360 parts water. The two solutions are mixed in a reaction vessel that contains 5000 parts water at 70° C. The reaction temperature is maintained at 70° C., and the pH is maintained at about 7.5. A precipitate is formed and recovered by vacuum filtration. It is then washed with water dried at 125° C. and calcined at 600° C. (±10° C.) for 45 minutes. The physical and chemical properties are given in Table II.

EXAMPLE C-8

A first solution is prepared as in Example 11 with the exception that 690 parts of an aqueous solution of aluminum nitrate containing about 2.7% aluminum is also added to it. The second solution is prepared from 650 parts of soda ash and 1600 parts water. The remainder of the procedure is the same as in Example 11.

EXAMPLE 12

The procedure is the same as in Example 11 except that 840 parts copper solution and 289 parts zinc solution are used in the first solution, and the second solution contains 305 parts sodium aluminate solution plus 320 parts soda ash.

EXAMPLE C-9

The procedure is the same as in Example 12 except that the first solution additionally contains 1185 parts aluminum nitrate solution. Also, second solution is prepared from 800 parts soda ash and 1500 parts water and contains no sodium aluminate.

EXAMPLE 13

The procedure is the same as in Example 11 except that 950 parts copper solution and 176 parts zinc solution are used in the first solution, and the second solution contains 704 parts sodium aluminate solution plus 154 parts soda ash.

EXAMPLE C-10

A first solution is prepared as in Example 13 with the exception that 2740 parts of an aqueous solution of aluminum nitrate containing about 2.7% aluminum is also added to it. The second solution is prepared from 1600 parts of soda ash and 3500 parts water. The remainder of the procedure is the same as in Example 11.

EXAMPLE 14

The procedure is the same as in Example 11 except that 488 parts copper solution and 637 parts zinc solution are used in the first solution, and the second solution contains 98 parts sodium aluminate solution plus 450 parts soda ash.

EXAMPLE C-11

A first solution is prepared as in Example 14 with the exception that 360 parts of an aqueous solution of aluminum nitrate containing about 2.7% aluminum is also added to it. The second solution is prepared from 550 parts of soda ash and 1300 parts water. The remainder of the procedure is the same as in Example 14.

Catalyst performance can be rated by different factors, the most common being activity and selectivity. Another important criterion for slurry-phase applications is catalyst filterability. As can be seen from the above examples of the invention, for catalysts of the present invention with a copper to zinc molar ratio of from about 0.5 to 5.5 and an aluminum content of greater than about 8 wt. percent, the size span from the smallest 10% of the particles to the largest 10% is between about 10 and about 45 microns, and averages about 25 microns. The median particle size for this composition range is from about 5 to about 20 microns and averages about 13 microns. In addition, for a copper to zinc molar ratio of less than 0.8 with an aluminum content greater than 3 wt. percent, the particle size span is from about 15 to about 20 microns and averages about 18 microns and the median particle size is from about 5 to about 20 microns and averages about 14 microns. These narrow particle size distributions result in catalysts with superior filtration properties, when compared to catalysts of similar composition that have been made by different prior art methods. Compare for example, the filtration rates reported for the product of Example 12 compared to C-9 reported in Table III.

The filtration test is carried out in a jacketed stainless steel pressure filter apparatus in the following manner. A temperature-controlled circulating water bath (which is connected to the filter jacket) is set to 60° C. The filter apparatus is assembled so that the filter medium, a porous membrane filter (such as Millipore type RA 1.2 $\mu$m) is supported by a fine stainless steel screen, and then the water circulation is started. The catalyst/product slurry to be filtered is preheated to 60° C. and poured into the filter. The top of the filter is then screwed on and sealed with buna-N rubber O-rings and pressured to 50 PSIG with nitrogen. A collection bottle is placed on a balance under the discharge port of the filter apparatus. The discharge port is then opened and a stopwatch is used to measure the time required to collect about 100, 200 and 300 grams of filtered product. The filtration rate (in grams per minute) is calculated by dividing the final weight collected by the time.

It is unusual to find a method of preparation that produces catalysts with superior performance over such a broad composition range. As can be seen from Example 14 and control example C-11, there is a small region

TABLE II

| | Example | | | | | | | |
|---|---|---|---|---|---|---|---|---|
| | 11 | C-8 | 12 | C-9 | 13 | C-10 | 14 | C-11 |
| Cu/Zn Molar Ratio | 0.551 | 0.50 | 2.85 | 2.81 | 5.31 | 5.13 | 0.77 | 0.75 |
| He Density (g/cc) | — | 4.85 | 4.69 | — | 4.27 | — | 4.99 | 4.86 |
| Hg Pore Vol. (cc/g)* | | | | | | | | |
| Pore Diameter (Å) | | | | | | | | |
| Up to 90 | — | 36.4 | 20.3 | — | 32.4 | — | 30.6 | 31.1 |
| Up to 120 | — | 64.8 | 21.0 | — | 47.3 | — | 38.7 | 65.2 |
| Up to 200 | — | 80.4 | 24.6 | — | 60.4 | — | 71.2 | 82.0 |
| Up to 350 | — | 90.5 | 34.9 | — | 71.2 | — | 84.7 | 92.5 |
| Up to 700 | — | 97.2 | 71.3 | — | 87.6 | — | 95.4 | 97.8 |
| Up to 1000 | — | 100 | 100 | — | 100 | — | 100 | 100 |
| Median Particle | | | | | | | | |
| Size ($\mu$m) | 18.8 | 19.7 | 16.8 | 74.5 | 9.8 | 95.1 | 17.8 | 12.1 |
| Size Span (90%–10%) | 18.5 | 23.1 | 29.9 | 129 | 42.6 | 134 | 21 | 11.8 |
| Chemical Analysis | | | | | | | | |
| at 500° C. (% wt) | | | | | | | | |
| Copper | 22.3 | 22.1 | 45.9 | 43.1 | 41.3 | 34.7 | 31.1 | 30.7 |
| Zinc | 44.7 | 44.7 | 16.3 | 15.4 | 7.9 | 6.9 | 40.9 | 41.7 |
| Aluminum | 7.7 | 6.9 | 10.9 | 10.6 | 19.2 | 16.5 | 3.3 | 3.5 |
| Sodium | 0.15 | 0.18 | 0.04 | 3.43 | 0.03 | 10.2 | 0.42 | 0.14 | of composition in which the catalysts of the present invention do not result in improved filtration performance (over the prior art), however, they do still exhibit superior activity (see Table III).

The catalysts of the present invention which contain copper, zinc and alumina have been found to be particularly useful for hydrogenating aldehydes, ketones, carboxylic acids and carboxylic esters to alcohols. Generally, these catalysts do not contain chromium or cobalt. In one embodiment, the atomic ratio of copper to zinc in the catalysts is from about 0.5 to 5.5, and in one preferred embodiment, the ratio is less than about 0.85, and the catalyst is also free of boron. In another preferred embodiment, the hydrogenation catalyst is characterized by an atomic ratio of copper to zinc of less than about 0.85, the catalyst is free of chromium, cobalt and boron, and the catalyst is prepared by the preferred process as illustrated in Examples 1-10.

The catalysts of the present invention which are prepared as powders may be utilized in slurry- (liquid-) phase hydrogenation processes. Alternatively, the powders can be processed into shapes such as pellets and used in fixed bed reactors. In one embodiment, carboxylic acids and carboxylic esters can be converted to alcohols in excellent yields. A wide variety of acids, particularly esters of carboxylic acids can be treated with the catalyst of the present invention to produce alcohols. The esters may be monoesters or diesters. Among the acids which may be hydrogenated to the corresponding alcohols without isolating the ester include stearic acids and caproic acids. Esters derived from the alcohols of higher molecular weight carboxylic acids are hydrogenated more rapidly and at lower temperatures than the esters derived from the lighter alcohols. Examples of esters which may be hydrogenated with the catalyst of the present invention include the methyl ester of coconut fatty acid, methyl stearate, methyl oleate, ethyl laurate, ethyl myristate, the diethyl ester of ethyl malonic acid, diethyl succinate, di-n-butyl glutarate, diethyl sebacate. As noted, the esters are converted to alcohols, and examples of such conversions include: ethyl laurate to lauryl alcohol; ethyl myristate to myristyl alcohol; ethyl valerate to n-amyl alcohol; methyl caproate to n-hexyl alcohol, etc.

Examples of aldehydes which may be hydrogenated with the catalyst of the present invention include: butyraldehyde, furfural, 2-ethylhexanal, dodecanal, tetradecanal, etc. Examples of ketones include acetone, acetophenone, etc.

The hydrogenation reactions which are conducted in the presence of the catalyst of the present invention are carried out at temperatures of from about 250° C. to about 350° C. and at pressures of from about 1500 psi to about 4500 psi.

In one preferred embodiment, the hydrogenation reaction is conducted in a batch or continuous ebullated bed reactor. In this process, the catalyst powder particles are slurried with the aldehyde, ketone, carboxylic acid or carboxylic ester to be reduced, and there is intimate contact between the catalyst and the liquid. When one of the preferred catalysts of the present invention wherein the atomic ratio of copper to zinc is less than about 0.85, and the catalyst is prepared by the preferred coprecipitation procedure such as illustrated in Examples 1-10, is used in a batch ebullated reactor, high yields of alcohols are obtained in shorter times, and the slurry, upon completion of the hydrogenation reaction is easily filtered.

Figure 1:
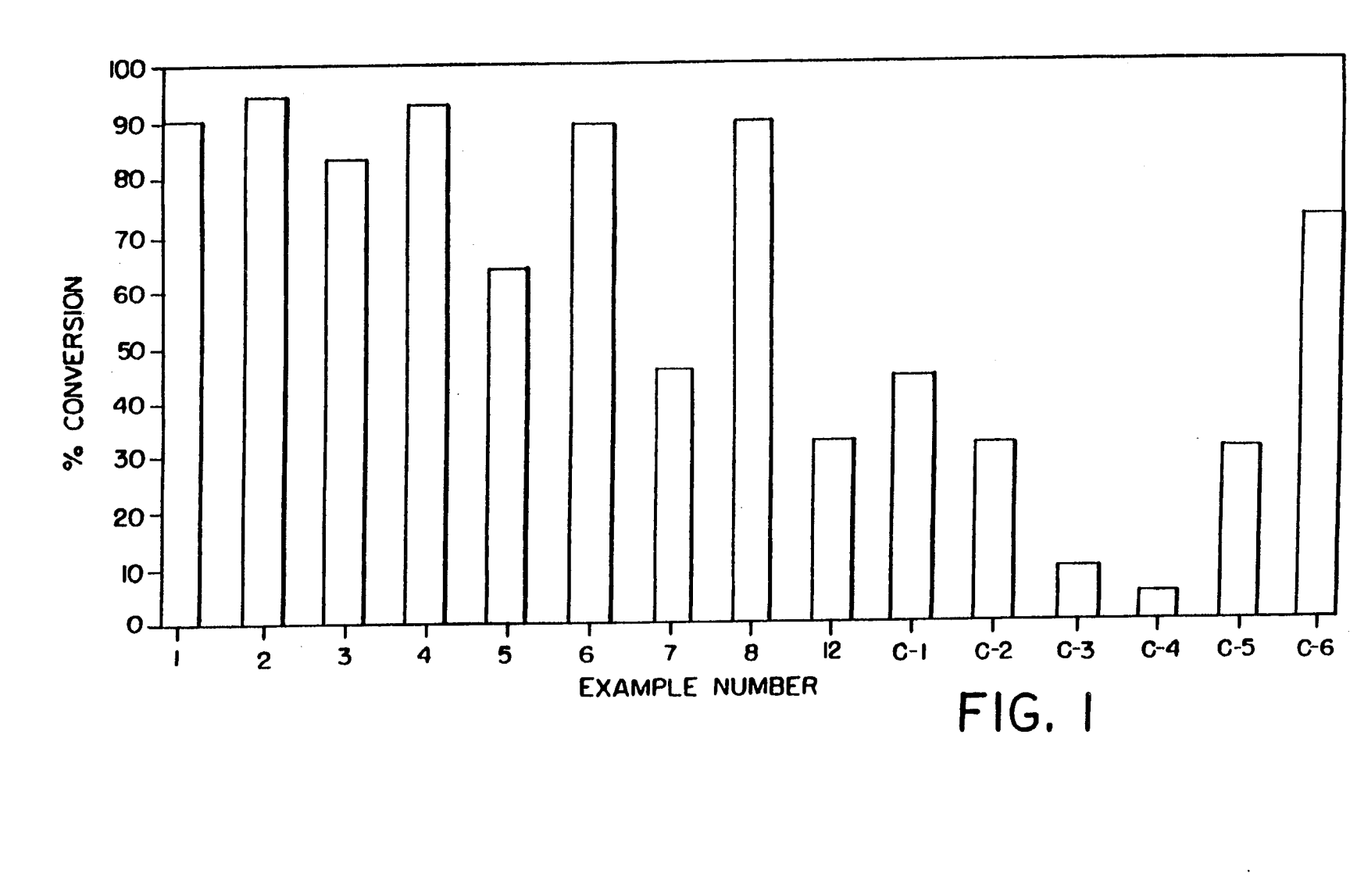
FIG. 1 is a graph illustrating the methyl ester hydrogenation activity of the catalyst prepared in Examples 1–7 as well as control examples C-1 to C-4, C-7 and a commercial catalyst C-6, with respect to percent conversion.

The effectiveness of the catalyst of Examples 1-7 of the present invention as hydrogenation catalysts is illustrated by utilizing the catalysts to hydrogenate coconut methyl-ester at 280° C., 3000 psig hydrogen and 1.8 weight percent catalyst loading, and measuring the percent conversion to the alcohol after the hydrogenation reaction has been conducted for 60 minutes. The results are summarized in the graph of FIG. 1. Also contained in FIG. 1 are the results of the hydrogenation reaction conducted with other catalysts which are not within the scope of the present invention which have been identified above as Examples C-1 to C-4, C-6 and C-7.

Figure 2:
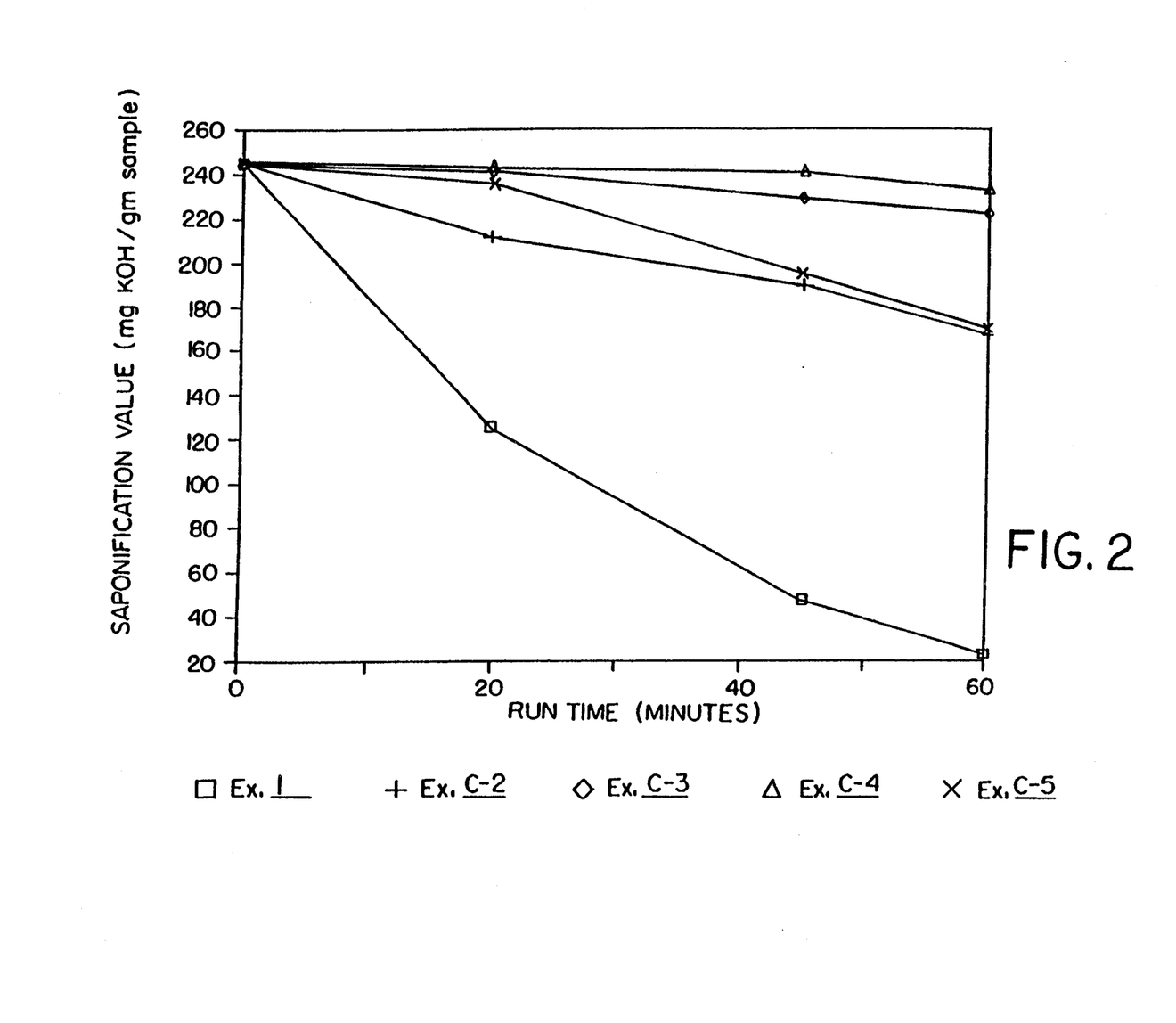
FIG. 2 is a graph illustrating the relative methyl ester hydrogenolysis activity (with respect to saponification value) of the catalyst of Example 1 compared to the activity of several catalysts containing other metal combinations.

The hydrogenation activity of the catalyst of Example 1 also has been compared to the catalysts of Examples C-2 through C-5 by carrying out hydrogenation reactions of coconut methyl ester at 280° C., 3000 psig of hydrogen and 1.8 weight percent catalyst loading. The effectiveness of the catalyst is determined by measuring the saponification values for each of the samples pursuant to A.O.C.S. official method Cd 3-25, revised April, 1966, reapproved 1973. Under these specific test conditions, saponification values of below about 50 indicate good hydrogenation activity. The results of this test are shown in FIG. 2, and the results demonstrate the improved hydrogenation activity of the catalyst of Example 1 when compared to the catalysts of Examples C-2 to C-5.

The process for hydrogenating a diester, namely, hydrodimethoxyterephthalate is illustrated as follows. The fixed-bed reaction is carried out using a pelletized version of a catalyst similar to that described in Example 9. The reaction is performed in an autoclave type reactor in which the catalyst is contained in a perforated, closed-ended tube known as a thimble and is in contact with the reaction medium. The reaction is carried out at about 250°-275° C., and about 2000-5000 psig of hydrogen. Catalytic activity is determined by measuring the percent conversion by gas chromatography. The catalyst of the present invention is at least 50% more active than commercial copper chromite catalysts.

TABLE III

| | Example | | | | | |
|---|---|---|---|---|---|---|
| | 1 | C-6 | 12 | C-9 | 14 | C-11 |
| Activity: Methyl-Ester Hydrogenolysis (% Conv) | 94 | 88 | 93 | 72 | 93 | 91 |
| Filtration Rate (g/min) | 15.2 | 7.0 | 4.0 | 1.0 | 1.7 | 4.9 |

An additional benefit of the present invention is that in those catalysts with aluminum contents above about 11 wt. percent, the residual sodium is easily washed out. For example, the catalysts of Example 13 and Control 10 were subjected to the same washing procedure, with the result that the catalyst of the present invention (Example 13) had a very low sodium level but the prior art catalyst (Control 10) had over 300 times as much residual sodium. (See Table II.) The presence of significant amounts of sodium ($\geq 2\%$) in the catalyst is detrimental to hydrogenation activity and results in the formation of difficult-to-reduce sodium salts of the organic acids and esters.

While the invention has been explained in relation to its preferred embodiments, it is to be understood that various modifications thereof will become apparent to those skilled in the art upon reading the specification. Therefore, it is to be understood that the invention disclosed herein is intended to cover such modifications as fall within the scope of the appended claims.

We claim:

1. In a process for hydrogenating aldehydes, ketones, carboxylic acids and carboxylic acid esters to alcohols comprising contacting the aldehyde, ketones, acid or ester with hydrogen and a catalyst under catalytic hydrogenation conditions, the improvement comprising using a catalyst in powdered form comprising a major amount of the oxides of copper and zinc, and a minor amount of aluminum oxide wherein the pore volume of the pores in said catalyst having a diameter of between about 120 and about 1000 Å is at least about 40% of the total pore volume.

2. The process of claim 1 wherein the pore volume of the pores in said catalyst having a diameter of greater than 120 Å is at least about 70% of the total pore volume.

3. The process of claim 1 wherein said catalyst powders have a surface area of at least 50 square meters per gram.

4. The process of claim 1 wherein said catalyst powders have an average particle diameter of from about 8 to about 30 microns.

5. The process of claim 1 wherein the atomic ratio of copper to zinc in said catalyst is about 0.2 to about 5.5.

6. The process of claim 1 wherein the atomic ratio of copper to zinc in said catalyst is from about 0.5 to about 3.0.

7. The process of claim 1 wherein the atomic ratio of copper to zinc in said catalyst is less than 1.

8. The process of claim 1 wherein the copper to zinc atomic ratio in said catalyst is less than about 0.85.

9. The process of claim 1 wherein the atomic ratio in of copper to zinc in said catalyst is from about 0.5 to about 0.85.

10. The process of claim 1 wherein the catalyst contains from about 3 to about 50% by weight of aluminum oxide.

11. The process of claim 1 wherein the atomic ratio of copper and zinc to aluminum in said catalyst is less than about 15.

12. The process of claim 1 wherein said catalyst is free of chromium and cobalt.

13. The process of claim 1 wherein said catalyst, for atomic ratios of copper to zinc from about 0.5 to 5.5 and an aluminum content greater than about 8 wt. percent, the particle size span from the smallest 10% of the particles to the largest 10% is between 10 and 45 microns.

14. The process of claim 1 wherein said catalyst, for atomic ratios of copper to zinc from about 0.5 to 5.5 and an aluminum content greater than about 8 wt. percent, the median particle size is between 5 and 20 microns.

15. The process of claim 1 wherein said catalyst, for atomic ratios of copper to zinc of greater than about 1.5 and an aluminum content greater than about 3 wt. percent, the particle size span is between 22 and 45 microns.

16. The process of claim 1 wherein said catalyst, for atomic ratios of copper to zinc of greater than about 1.5 and an aluminum content greater than about 3 wt. percent, the median particle size is between 8 and 25 microns.

17. In a process for hydrogenating carboxylic acid esters to alcohols comprising contacting the ester with hydrogen and a catalyst under catalytic hydrogenation conditions, the improvement comprising using a catalyst in powdered form comprising the oxides of copper, zinc and aluminum wherein the atomic ratio of copper to zinc is less than about 0.85, provided that the catalyst does not contain chromium, boron or cobalt, wherein the pore volume of the pores in said catalyst having a diameter of between about 120 and about 1000 Å is at least about 40% of the total pore volume.

18. The process of claim 17 wherein the pore volume of pores in the catalyst having a diameter of greater than 120 Å is at least about 70% of the total pore volume.

19. The process of claim 17 conducted in the liquid phase.

* * * * *

UNITED STATES PATENT AND TRADEMARK OFFICE
CERTIFICATE OF CORRECTION

PATENT NO. : 5,345,005
DATED : September 6, 1994
INVENTOR(S) : Thakur, et al

It is certified that error appears in the above-indentified patent and that said Letters Patent is hereby corrected as shown below:

On the title page, item [75] should read as follow:

Inventors: Deepak S. Thakur; Brian D. Roberts, both of Solon; Thomas J. Sullivan, Strongsville; Anita L. Vlchek, Mentor; all of Ohio Signed and Sealed this Twentieth Day of December, 1994

*Attest:*

BRUCE LEHMAN

*Attesting Officer*      *Commissioner of Patents and Trademarks*